US012144564B2

(12) United States Patent
Barbagli et al.

(10) Patent No.: US 12,144,564 B2
(45) Date of Patent: Nov. 19, 2024

(54) SYSTEMS AND METHODS FOR REGISTERING AN INSTRUMENT TO AN IMAGE USING CHANGE IN INSTRUMENT POSITION DATA

(71) Applicant: INTUITIVE SURGICAL OPERATIONS, INC., Sunnyvale, CA (US)

(72) Inventors: Federico Barbagli, San Francisco, CA (US); Troy K. Adebar, San Jose, CA (US); Sungwon Yoon, Palo Alto, CA (US); Hui Zhang, San Jose, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 379 days.

(21) Appl. No.: 17/774,797

(22) PCT Filed: Nov. 5, 2020

(86) PCT No.: PCT/US2020/059025
§ 371 (c)(1),
(2) Date: May 5, 2022

(87) PCT Pub. No.: WO2021/092116
PCT Pub. Date: May 14, 2021

(65) Prior Publication Data
US 2022/0387115 A1 Dec. 8, 2022

Related U.S. Application Data

(60) Provisional application No. 62/932,858, filed on Nov. 8, 2019.

(51) Int. Cl.
*A61B 34/20* (2016.01)
*A61B 17/00* (2006.01)
(Continued)

(52) U.S. Cl.
CPC .............. *A61B 34/20* (2016.02); *A61B 34/10* (2016.02); *A61B 34/37* (2016.02); *G06T 7/20* (2013.01);
(Continued)

(58) Field of Classification Search
CPC ......... A61B 34/20; A61B 34/10; A61B 34/37; A61B 2017/00809; A61B 2034/105;
(Continued)

(56) References Cited

U.S. PATENT DOCUMENTS 10,582,909 B2 * 3/2020 Donhowe ............... A61B 10/04
10,898,275 B2 * 1/2021 Ye ......................... A61B 1/2676
(Continued)

FOREIGN PATENT DOCUMENTS

| CN | 107660134 B | * | 6/2021 | ......... A61B 1/00009 |
| WO | WO-9859219 A2 | * | 12/1998 | ............. G01D 5/353 |

(Continued)

OTHER PUBLICATIONS

International Search Report and Written Opinion for Application No. PCT/US2020/059025, mailed Apr. 22, 2021, 22 pages.
(Continued)

*Primary Examiner* — Mahendra R Patel
(74) *Attorney, Agent, or Firm* — Haynes & Boone, LLP.

(57) ABSTRACT

A system may comprise a processor and a memory having computer readable instructions stored thereon. The computer readable instructions, when executed by the processor, cause the system to record position data for an instrument during an image capture period and determine an instrument position change from the recorded position data. The computer readable instructions, when executed by the processor, may also cause the system to compare the instrument position change to a position change threshold and based on the comparison, determine whether to use image data cap- (Continued)

tured by an imaging system during the image capture period in a registration procedure.

20 Claims, 6 Drawing Sheets

(51) Int. Cl.
    *A61B 34/10* (2016.01)
    *A61B 34/30* (2016.01)
    *A61B 34/37* (2016.01)
    *A61B 90/00* (2016.01)
    *G06T 7/20* (2017.01)
    *G06T 7/50* (2017.01)
    *G06T 7/70* (2017.01)
    *G06V 10/74* (2022.01)

(52) U.S. Cl.
    CPC ............... *G06T 7/50* (2017.01); *G06T 7/70* (2017.01); *G06V 10/761* (2022.01); *A61B 2017/00809* (2013.01); *A61B 2034/105* (2016.02); *A61B 2034/2051* (2016.02); *A61B 2034/2061* (2016.02); *A61B 2034/301* (2016.02); *A61B 2090/3764* (2016.02)

(58) Field of Classification Search
    CPC .... A61B 2034/2051; A61B 2034/2061; A61B 2034/301; A61B 2090/3764; G06T 7/20; G06T 7/50; G06T 7/70; G06V 10/761
    USPC ........................................................ 382/103
    See application file for complete search history.

(56) References Cited

U.S. PATENT DOCUMENTS

| | | | |
|---|---|---|---|
| 11,490,782 B2 * | 11/2022 | Rafii-Tari | A61B 34/35 |
| 11,523,749 B2 * | 12/2022 | Schwartz | A61B 5/066 |
| 11,547,490 B2 * | 1/2023 | Wang | A61B 34/10 |
| 11,622,689 B2 * | 4/2023 | Malchano | A61B 5/0245 600/407 |
| 11,628,013 B2 * | 4/2023 | Gadda | A61B 34/20 606/130 |
| 11,744,654 B2 * | 9/2023 | Rohr Daniel | A61B 1/0016 74/490.05 |
| 11,931,141 B2 * | 3/2024 | Averbuch | A61B 1/2676 |
| 2006/0013523 A1 | 1/2006 | Chidlers | |
| 2008/0212082 A1 | 9/2008 | Froggatt | |
| 2009/0262980 A1 * | 10/2009 | Markowitz | G06V 20/64 382/128 |
| 2009/0268010 A1 * | 10/2009 | Zhao | A61B 1/00194 348/E13.001 |
| 2010/0249506 A1 * | 9/2010 | Prisco | A61B 1/0051 600/117 |
| 2017/0265956 A1 * | 9/2017 | Carlson | A61B 34/77 |
| 2018/0235709 A1 | 8/2018 | Donhowe | |
| 2018/0240237 A1 | 8/2018 | Donhowe | |
| 2019/0239723 A1 | 8/2019 | Duindam et al. | |

FOREIGN PATENT DOCUMENTS

| | | | | |
|---|---|---|---|---|
| WO | WO-2007067323 A2 * | 6/2007 | | A61B 8/445 |
| WO | WO-2007146987 A2 * | 12/2007 | | A61B 1/00087 |
| WO | WO-2018038999 A1 * | 3/2018 | | A61B 34/20 |
| WO | WO-2018085287 A1 * | 5/2018 | | A61B 1/000094 |

OTHER PUBLICATIONS

Invitation to pay additional fee received from the International Search Authority for Application No. PCT/US2020/059025, mailed Mar. 1, 2021, 15 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2020/059025, mailed May 19, 2022, 14 pages.

* cited by examiner

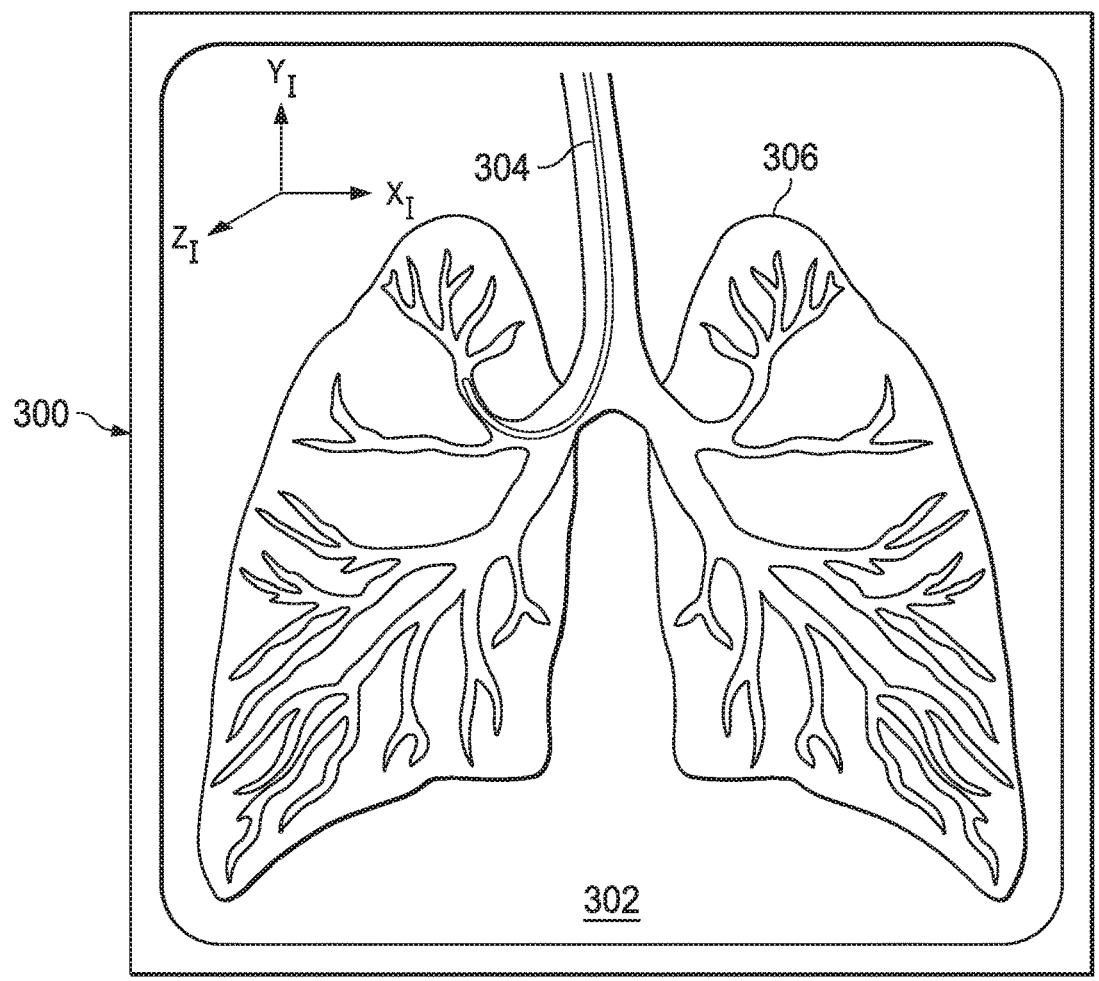
Fig. 3
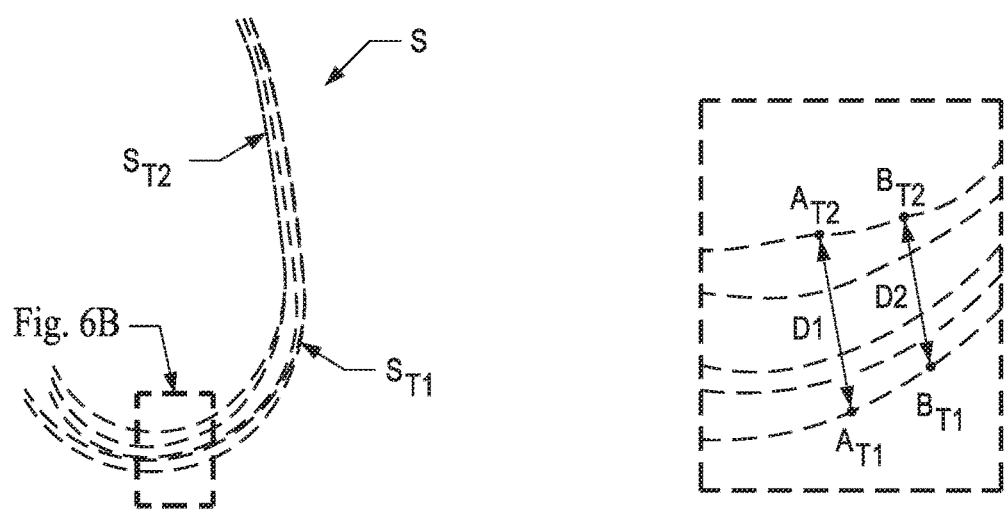
Fig. 6A
Fig. 6B

SYSTEMS AND METHODS FOR REGISTERING AN INSTRUMENT TO AN IMAGE USING CHANGE IN INSTRUMENT POSITION DATA

CROSS-REFERENCE TO RELATED APPLICATIONS

This application is the U.S. national phase of International Application No. PCT/US2020/059025, filed Nov. 5, 2020, which designated the U.S. and claims priority to and the benefit of U.S. Provisional Application No. 62/932,858, filed Nov. 8, 2019, both of which are incorporated by reference herein in their entirety.

FIELD

The present disclosure is directed to systems and methods for registering instrument and image frames of reference.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform registrations between medical tools and images of the anatomic passageways.

SUMMARY

Consistent with some embodiments, a system may comprise a processor and a memory having computer readable instructions stored thereon. The computer readable instructions, when executed by the processor, cause the system to record position data for an instrument during an image capture period and determine an instrument position change from the recorded position data. The computer readable instructions, when executed by the processor, may also cause the system to compare the instrument position change to a position change threshold and based on the comparison, determine whether to use image data captured by an imaging system during the image capture period in a registration procedure.

Consistent with some embodiments, a non-transitory machine-readable medium may comprise a plurality of machine-readable instructions which when executed by one or more processors associated with a computer-assisted medical system device are adapted to cause the one or more processors to perform a method that may comprise recording position data for an instrument during an image capture period and determining an instrument position change from the recorded position data. The performed method may also comprise comparing the instrument position change to a position change threshold and based on the comparison, determining whether to use image data captured by an imaging system during the image capture period in a registration procedure.

Consistent with some embodiments, a system may comprise a processor and a memory having computer readable instructions stored thereon. The computer readable instructions, when executed by the processor, may cause the system to record shape data for an instrument positioned in a patient anatomy and compare an instrument shape determined from the shape data to a registration shape threshold. Based on the comparison, the system may determine whether to initiate an image capture procedure to capture an image of the patient anatomy and the instrument.

Consistent with some embodiments, a clinical system may comprise a medical system including a shape sensor and an imaging system in communication with the medical system. The clinical system may also comprise a processor and a memory having computer readable instructions stored thereon. The computer readable instructions, when executed by the processor, may cause the clinical system to generate a communication signal including synchronization information and send the communication signal between the medical system and the imaging system. Based on the synchronization information, the clinical system may synchronize recording of shape data from the shape sensor with recording of image data from the imaging system during an image capture period.

Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 3 illustrates a display system displaying an image of a medical instrument registered to an anatomical image.

FIG. 6A illustrates a plurality of points forming a shape of the medical instrument.

FIG. 6B illustrates a detailed view of a section of the plurality of points of FIG. 6A.

Figure 1A:
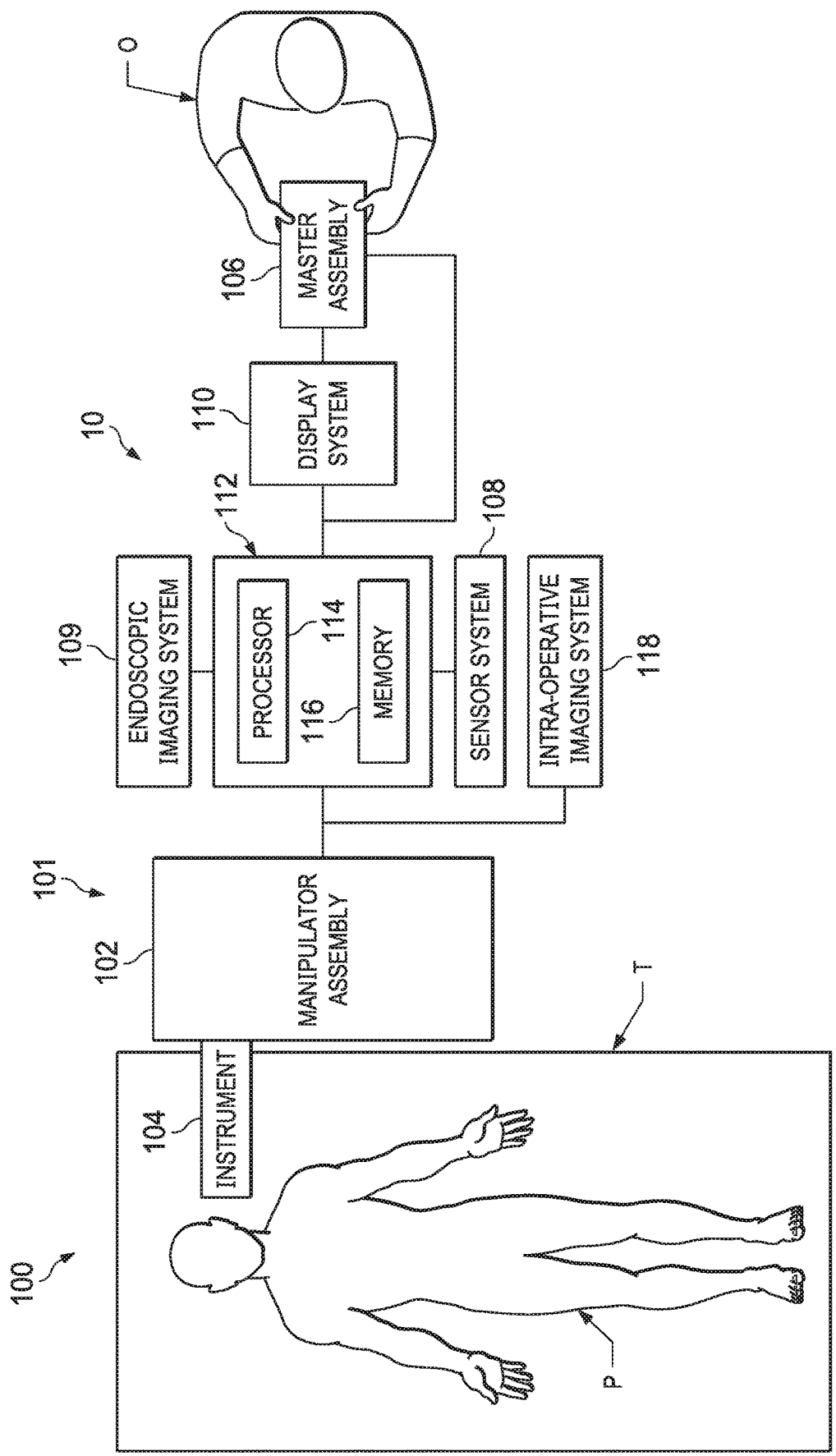
FIG. 1A illustrates a simplified diagram of a robotic or teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The techniques disclosed in this document may be used to register a medical instrument reference frame to an image frame of reference for an intra-operative image that includes an image of the medical instrument. Often, anatomical motion can result in intra-operative images that are too distorted to isolate and segment the catheter. Before attempting to register the intra-operative image to the medical instrument, a change in the shape and position of the medical instrument may be evaluated over the image capture period. If the shape of the medical instrument changes in excess of a threshold amount, the captured image may be considered inadequate for use in registration, and instructions may be provided to initiate a new image capture procedure.

In some embodiments, the registration techniques of this disclosure may be used in an image-guided medical procedure performed with a teleoperated medical system as described in further detail below. As shown in FIG. 1a, a clinical system 10 includes a tele-operated medical system 100 and an intra-operative imaging system 118. The tele-operated medical system 100 generally includes a manipulator assembly 102 for operating a medical instrument system 104 in performing various procedures on a patient P positioned on a table T in a surgical environment 101. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. A master assembly 106, which may be inside or outside of the surgical environment 101, generally includes one or more control devices for controlling manipulator assembly 102. Manipulator assembly 102 supports medical instrument system 104 and may optionally include a plurality of actuators or motors that drive inputs on medical instrument system 104 in response to commands from a control system 112. The actuators may optionally include drive systems that when coupled to medical instrument system 104 may advance medical instrument system 104 into a naturally or surgically created anatomic orifice. Other drive systems may move the distal end of medical instrument system 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument system 104 for grasping tissue in the jaws of a biopsy device and/or the like.

Teleoperated medical system 100 also includes a display system 110 for displaying an image or representation of the surgical site and medical instrument system 104 generated by a sensor system 108 and/or an endoscopic imaging system 109. Display system 110 and master assembly 106 may be oriented so operator O can control medical instrument system 104 and master assembly 106 with the perception of telepresence.

In some embodiments, medical instrument system 104 may include components for use in surgery, biopsy, ablation, illumination, irrigation, or suction. Optionally medical instrument system 104, together with sensor system 108 may be used to gather (i.e., measure) a set of data points corresponding to locations within anatomic passageways of a patient, such as patient P. In some embodiments, medical instrument system 104 may include components of the imaging system 109, which may include an imaging scope assembly or imaging instrument that records a concurrent or real-time image of a surgical site and provides the image to the operator or operator O through the display system 110. The concurrent image may be, for example, a two or three-dimensional image captured by an imaging instrument positioned within the surgical site. In some embodiments, the imaging system components that may be integrally or removably coupled to medical instrument system 104. However, in some embodiments, a separate endoscope, attached to a separate manipulator assembly may be used with medical instrument system 104 to image the surgical site. The imaging system 109 may be implemented as hardware, firmware, software or a combination thereof which interact with or are otherwise executed by one or more computer processors, which may include the processors of the control system 112.

The sensor system 108 may include a position/location sensor system (e.g., an electromagnetic (EM) sensor system) and/or a shape sensor system for determining the position, orientation, speed, velocity, pose, and/or shape of the medical instrument system 104.

Teleoperated medical system 100 may also include control system 112. Control system 112 includes at least one memory 116 and at least one computer processor 114 for effecting control between medical instrument system 104, master assembly 106, sensor system 108, endoscopic imaging system 109, and display system 110. Control system 112 also includes programmed instructions (e.g., a non-transitory machine-readable medium storing the instructions) to implement some or all of the methods described in accordance with aspects disclosed herein, including instructions for providing information to display system 110.

Control system 112 may optionally further include a virtual visualization system to provide navigation assistance to operator O when controlling medical instrument system 104 during an image-guided surgical procedure. Virtual navigation using the virtual visualization system may be based upon reference to an acquired pre-operative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

An intra-operative imaging system 118 may be arranged in the surgical environment 101 near the patient P to obtain images of the patient P during a medical procedure. The intra-operative imaging system 118 may provide real-time or near real-time images of the patient P. In some embodiments, the system 118 may be a mobile C-arm cone-beam CT imaging system for generating three-dimensional images. For example, the system 118 may be a DynaCT imaging system from Siemens Corporation of Washington, D.C., or other suitable imaging system. In other embodiments, the imaging system may use other imaging technologies including CT, MRI, fluoroscopy, thermography, ultrasound, optical coherence tomography (OCT), thermal imaging, impedance imaging, laser imaging, nanotube X-ray imaging, and/or the like.

Figure 1B:
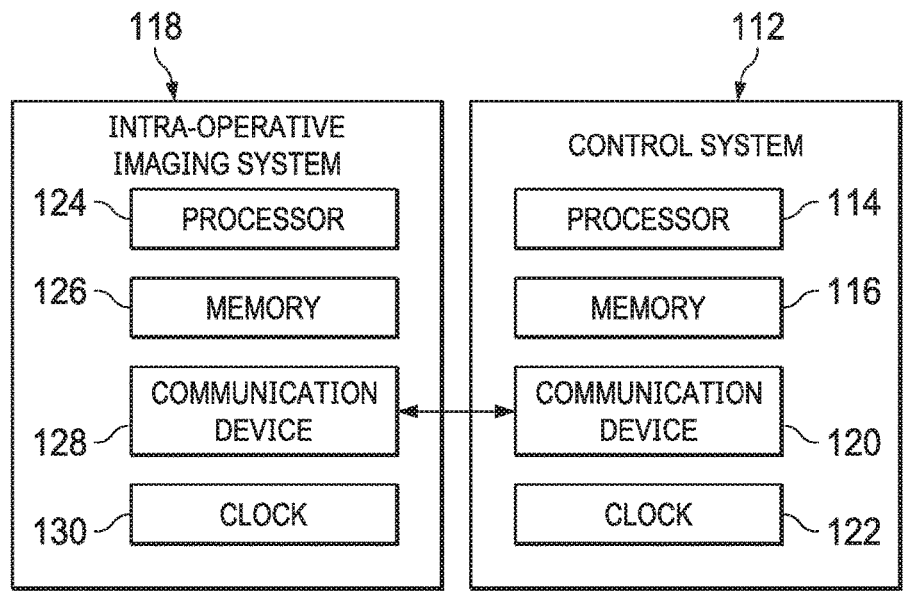
FIG. 1B illustrates communication between a control system and an intra-operative imaging system.

FIG. 1b illustrates communication between the control system 112 and the intra-operative imaging system 118. In some embodiments, the control system 112 includes a communication device 120 and a clock 122. Although the control system 112 is shown as a single block in the simplified schematics of FIGS. 1a and 1b, the control system 112 may include multiple processors, memories, communication devices, and clocks. Furthermore, the components of the control system 112 may be distributed throughout the medical system 100, including at the manipulator assembly 102, the instrument system 104 and the master assembly 106. In some embodiments, the intra-operative imaging system includes a processor 124, a memory 126, a communication device 128, and a clock 130. The processor 124 is configured to execute programmed instructions stored, for example, on memory 126 to implement some or all of the methods described in accordance with aspects disclosed herein. The clocks 122, 130 may include any type of digital clock, analog clock, software-based clock, or other timekeeping device. The communication devices 120, 128 may include information transmitters, information receivers, information transceivers or a combination of transmitting or receiving devices that enable wired or wireless communication between the imaging system 118 and the control system 112 and/or between the clocks 122, 130. The communication devices 120, 128 may be used to exchange information between the two systems including, for example, clock signals, start and stop signals, image data signals, patient data signals, and sensor data signals.

Figure 2:
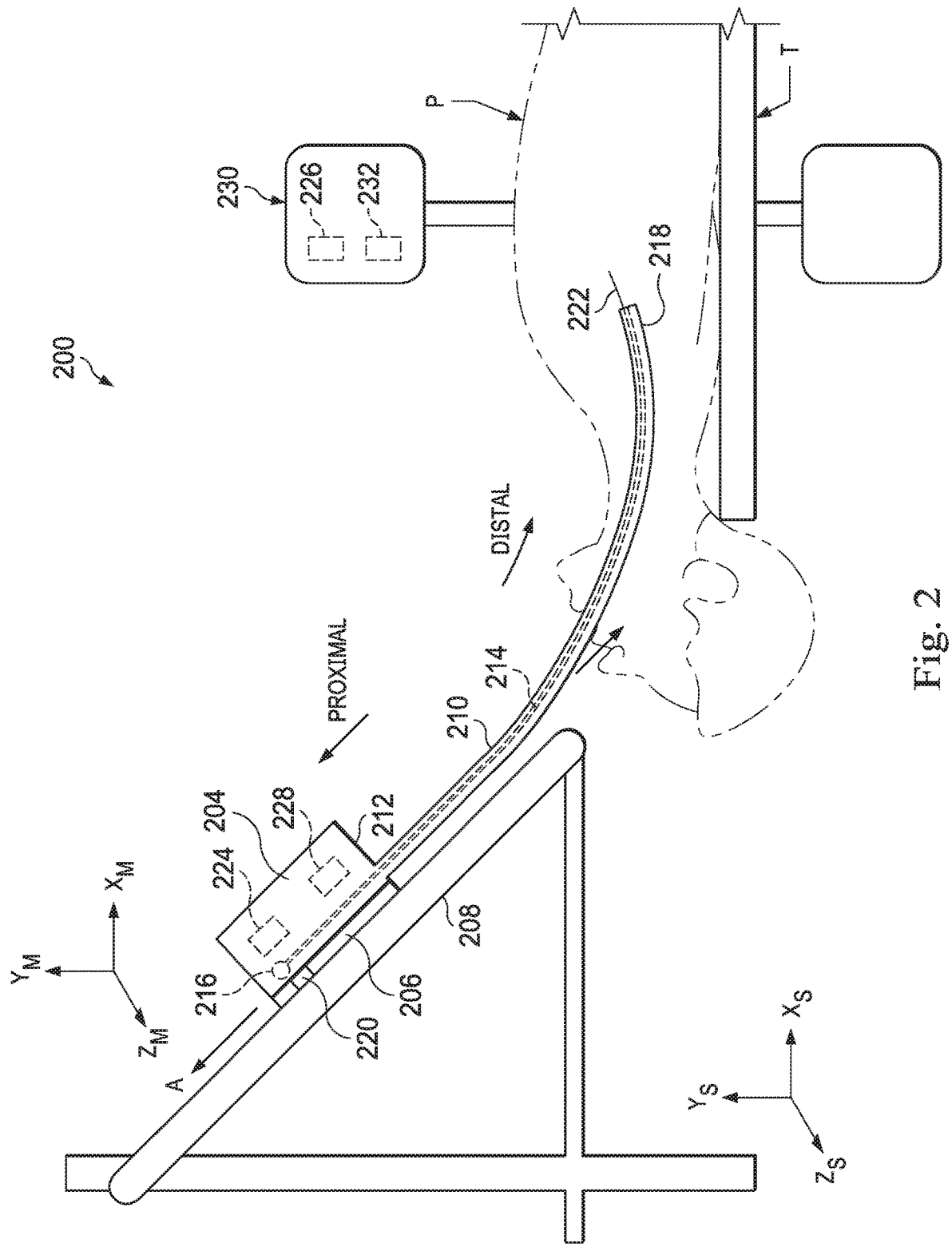
FIG. 2 illustrates a simplified diagram of a medical instrument system and an intraoperative imaging system according to some embodiments.

FIG. 2 illustrates a surgical environment 200 with a surgical frame of reference ($X_S$, $Y_S$, $Z_S$) in which the patient P is positioned on the table T. Patient P may be stationary within the surgical environment in the sense that gross patient movement is limited by sedation, restraint, and/or other means. Cyclic anatomic motion including respiration and cardiac motion of patient P may continue unless the patient is asked to hold his or her breath to temporarily suspend respiratory motion. Within surgical environment 200, a medical instrument 204 (e.g., the medical instrument system 104), having a medical instrument frame of reference ($X_M$, $Y_M$, $Z_M$), is coupled to an instrument carriage 206. In this embodiment, medical instrument 204 includes an elongate device 210, such as a flexible catheter, coupled to an instrument body 212. Instrument carriage 206 is mounted to an insertion stage 208 fixed within surgical environment 200. Alternatively, insertion stage 208 may be movable but have a known location (e.g., via a tracking sensor or other tracking device) within surgical environment 200. In these alternatives, the medical instrument frame of reference is fixed or otherwise known relative to the surgical frame of reference. Instrument carriage 206 may be a component of a teleoperational manipulator assembly (e.g., teleoperational manipulator assembly 102) that couples to medical instrument 204 to control insertion motion (i.e., motion along an axis A) and, optionally, motion of a distal end 218 of the elongate device 210 in multiple directions including yaw, pitch, and roll. Instrument carriage 206 or insertion stage 208 may include actuators, such as servomotors, (not shown) that control motion of instrument carriage 206 along insertion stage 208.

In this embodiment, a sensor system (e.g., sensor system 108) includes a shape sensor 214. Shape sensor 214 may include an optical fiber extending within and aligned with elongate device 210. In one embodiment, the optical fiber has a diameter of approximately 200 μm. In other embodiments, the dimensions may be larger or smaller. The optical fiber of shape sensor 214 forms a fiber optic bend sensor for determining the shape of the elongate device 210. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the catheter may be determined using other techniques. For example, a history of the distal end pose of elongate device 210 can be used to reconstruct the shape of elongate device 210 over the interval of time.

As shown in FIG. 2, instrument body 212 is coupled and fixed relative to instrument carriage 206. In some embodiments, the optical fiber shape sensor 214 is fixed at a proximal point 216 on instrument body 212. In some embodiments, proximal point 216 of optical fiber shape sensor 214 may be movable along with instrument body 212 but the location of proximal point 216 may be known (e.g., via a tracking sensor or other tracking device). Shape sensor 214 measures a shape from proximal point 216 to another point such as distal end 18 of elongate device 210 in the medical instrument reference frame ($X_M$, $Y_M$, $Z_M$).

Elongate device 210 includes a channel (not shown) sized and shaped to receive a medical instrument 222. In some embodiments, medical instrument 222 may be used for procedures such as surgery, biopsy, ablation, illumination, irrigation, or suction. Medical instrument 222 can be deployed through elongate device 210 and used at a target location within the anatomy. Medical instrument 222 may include, for example, image capture probes, biopsy instruments, laser ablation fibers, and/or other surgical, diagnostic, or therapeutic tools. Medical instrument 222 may be advanced from the distal end 218 of the elongate device 210 to perform the procedure and then retracted back into the channel when the procedure is complete. Medical instrument 222 may be removed from proximal end of elongate device 210 or from another optional instrument port (not shown) along elongate device 210.

Elongate device 210 may also house cables, linkages, or other steering controls (not shown) to controllably bend distal end 218. In some examples, at least four cables are used to provide independent "up-down" steering to control a pitch of distal end 218 and "left-right" steering to control a yaw of distal end 218.

A position measuring device 220 provides information about the position of instrument body 212 as it moves on insertion stage 208 along an insertion axis A. Position measuring device 220 may include resolvers, encoders, potentiometers, and/or other sensors that determine the rotation and/or orientation of the actuators controlling the motion of instrument carriage 206 and consequently the motion of instrument body 212. In some embodiments, insertion stage 208 is linear, while in other embodiments, the insertion stage 208 may be curved or have a combination of curved and linear sections.

An intra-operative imaging system 230 (e.g., imaging system 118) is arranged near the patient P to obtain three-dimensional images of the patient while the elongate device 210 is extended within the patient. The intra-operative imaging system 230 may provide real-time or near real-time images of the patient P.

In some embodiments, the medical instrument 204 or another component of a teleoperated medical system registered to the medical instrument 204 may include an instrument clock 224 (e.g., clock 122 of a distributed control system 112). The imaging system 230 may include an imaging clock 226 (e.g., clock 130). The clocks 224, 226 may be time synchronized on a predetermined schedule or in response to a synchronization initiation event generated by a user, a control system, or a synchronization system. In some embodiments, the clocks 224, 226 may be components of a synchronization system that may be a centralized or distributed system further comprising servers, wired or wireless communication networks, communication devices, or other components for executing synchronization algorithms and protocols. In some embodiments, the medical instrument 204 or another component of a tele-operated medical system registered to the medical instrument 204 may include a communication device 228 (e.g., communication device 120 of a distributed control system 112). The imaging system 230 may include a communication device 232 (e.g., communication device 128 of the imaging system 118).

In some embodiments and with reference to FIG. 3, an image guided surgical procedure may be conducted in which the display system 300 (e.g., the display system 110) may display a virtual navigational image 302, having an image reference frame ($X_I$, $Y_I$, $Z_I$) in which an image 304 of the medical instrument 204 is registered (i.e., dynamically referenced) with an anatomic model 306 of patient P derived from preoperative and/or intraoperative image data. In some embodiments, a virtual navigational image may present the physician O with a virtual image of the internal surgical site from a viewpoint of medical instrument 204. In some examples, the viewpoint may be from a distal tip of medical instrument 204. In some examples, medical instrument 204 may not be visible in the virtual image.

Generating the composite virtual navigational image 302 involves the registration of the image reference frame ($X_I$, $Y_I$, $Z_I$) to the surgical reference frame ($X_S$, $Y_S$, $Z_S$) and/or medical instrument reference frame ($X_M$, $Y_M$, $Z_M$). This registration may rotate, translate, or otherwise manipulate by rigid or non-rigid transforms points associated with the segmented instrument shape from the image data and points associated with the shape data from the instrument shape sensor 214. This registration between the image and instrument frames of reference may be achieved, for example, by using a point-based iterative closest point (ICP) technique as described in incorporated by reference U.S. Provisional Pat. App. Nos. 62/205,440 and No. 62/205,433, or another point cloud registration technique.

Figure 4:
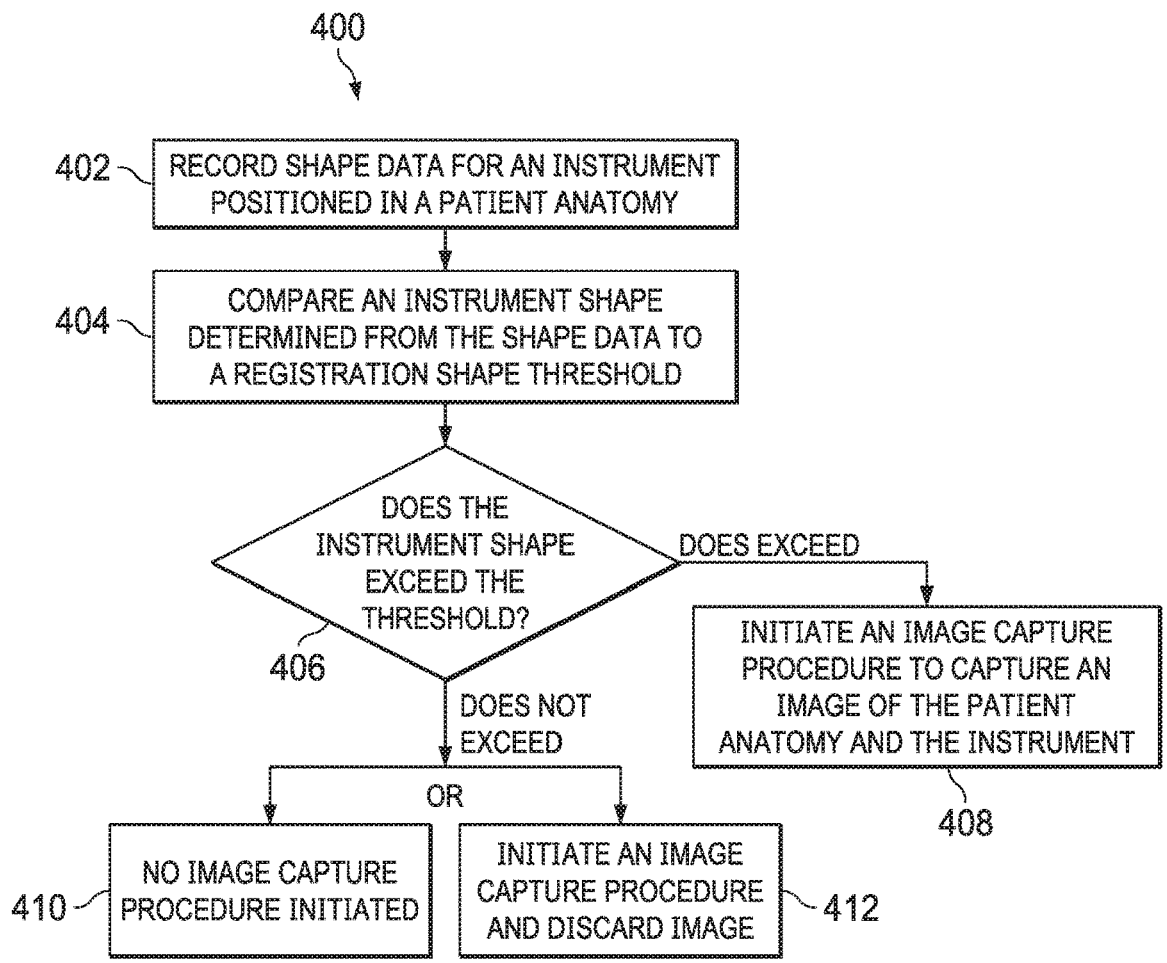
FIG. 4 illustrates a method for evaluating the shape of a medical instrument to determine whether an intra-operative imaging procedure should be performed

FIG. 4 illustrates a method 400 for evaluating the shape of a medical instrument to determine whether an intra-operative imaging procedure should be performed, particularly when administration of the imaging procedure will expose the patient P to radiation. As compared to a medical instrument configured in a straight configuration, shape data from a medical instrument configured with bends in each of the three dimensions may be particularly useful in three-dimensional registration with anatomic image data.

At a process 402, shape data is recorded for an instrument (e.g., medical instrument system 104, 204) while the instrument is located in the anatomy of a patient P. For example, shape data, gathered from shape sensor 214, may provide shape information for the instrument 204, including position and orientation information for a plurality of points along the instrument 204.

At a process 404, the recorded instrument shape data is compared to a registration shape threshold. In some embodiments, the registration shape threshold may be a curvature threshold corresponding to a shape that includes a bend in at least one or two of three dimensions in a three-dimensional environment. In some embodiments, the registration shape threshold may be a shape that includes a bend in all three dimensions of the three-dimensional environment. In this example, any viewing plane in the three-dimensional environment will include a curved shape that allows for a full three-dimensional registration.

At a process 406, based on the comparison, a determination is made as to whether the instrument shape determined from the shape data exceeds the registration shape threshold.

At a process 408, if the recorded instrument shape does exceed the registration shape threshold, the shape of the instrument 204 may be considered sufficiently curved to permit image capture. An image capture procedure may be initiated to capture an image of the patient anatomy and the instrument. For example, an initiation signal may be sent from communication device 120 of the control system 112 to the communication device 128 of the imaging system 118 to initiate an image capture procedure with the imaging system.

At a process 410, if the recorded instrument shape does not exceed the registration shape threshold, the shape of the instrument 204 may be considered insufficiently curved or too straight to permit image capture. The image capture procedure is not initiated, and no initiation signal is sent from the control system 112 to the imaging system 118. In some embodiments, instructions may be provided to alert the user that the image capture procedure was not initiation and the reason why it was not initiated. For example, instructions may be provided through text or images displayed on a user interface such as the display system 110, through audio messages sent to the user, or through other types of communication perceptible by the user. In some embodiments, a textual message such as "Image capture not initiated. Instrument curvature does not meet the bend threshold." in some embodiments, corrective instructions may be further provided. For example, textual instructions may be provided to bend the instrument or otherwise reconfigure the instrument until a bend sufficient to exceed the threshold is reached. Additionally or alternatively, a guidance image may be provided to guide the user to bend the instrument to generate a shape as shown in the guidance image.

At a process 412 that may be an alternative process to process 410, an image capture procedure may be initiated to capture an image of the patient anatomy and the instrument. For example, an initiation signal may be sent from communication device 120 of the control system 112 to the communication device 128 of the imaging system 118 to initiate an image capture procedure with the imaging system. The captured image may then be discarded, suppressed or otherwise not used in a registration procedure.

In some embodiments, a determination may be made as to the location of the curvature that exceeds the registration shape threshold. Based on the location of the curvature, a determination may be made as to whether an image of the patient anatomy will include the image of the curvature. If the field of view of the imaging system will not include the curvature, the image capture procedure may not be initiated. The medical instrument may be rearranged until it forms a curvature, within the field of view of the imaging system, that exceeds the curvature threshold. Additionally or alternatively, instructions may be sent to a user to move the imaging system to a different imaging position or imaging orientation to capture an image of the patient anatomy that will include an image of the curvature that exceeds the registration shape threshold.

Figure 5:
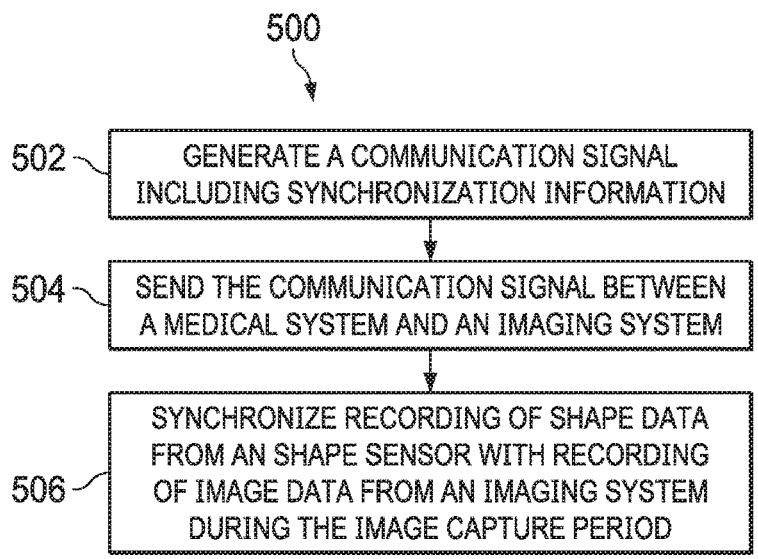
FIG. 5 illustrates a method for synchronizing a teleoperated medical system with an imaging system during an image capture period of the imaging system.

FIG. 5 illustrates a method 500 for synchronizing a teleoperated medical system (e.g., system 100) with an imaging system (e.g., imaging system 230) during an image capture period of the imaging system. During the synchronized image capture period, two different representations of a physical entity, for example the medical instrument 204, may be recorded. One representation may be the three-dimensional image of the instrument generated by the imaging system, and one representation may be the three-dimensional shape generated by the shape sensor.

At a process 502, a communication signal is generated. The communication signal includes synchronization information which may include start and/or stop signals, clock signals, synchronization protocol information, image capture period duration information, or other information for synchronizing a medical system and an imaging system. For example, the communication signal may be generated by the communication device 120 of the control system 112 or by the communication device 128 of the imaging system.

At a process 504, the communication signal is sent between the medical system and the imaging system. For example, the communication signal may be sent from the communication device 120 to the communication device 128 or from the communication device 128 to the communication device 120.

At a process 506, based on the synchronization information from the communication signal, the recording of shape data from an instrument shape sensor of the medical system is synchronized with the recording of image data from the imaging system during an image capture period. Because the medical and imaging systems are synchronized, the image data and the shape data are recorded over the same period of time. Both the shape data and the image data may be recorded while the medical instrument, including the instrument shape sensor, is located within the imaged anatomy of the patient. With the data collection periods for the shape sensor and the imaging system synchronized, two different representations of the medical instrument are recorded. The image data, including an image of the shape of the instrument, can be matched to the shape sensor data, describing the shape of the same instrument, for the exact same time period. As described further below, the matched data sets may be used for registration of the image reference frame $(X_I, Y_I, Z_I)$ with the medical instrument reference frame $(X_M, Y_M, Z_M)$.

In one embodiment, the clock 122 of the medical system is synchronized to the clock 130 of the imaging system during an image capture period. A communication signal including synchronization information for synchronizing the clocks 122, 130 may be sent between the medical system 100 and the imaging system 118. In some examples, the synchronization information includes signals from clock 122 that are sent from the communication device 120 to the communication device 128 for synchronizing with clock 130. In other examples, the synchronization information includes signals from clock 130 that are sent from the communication device 128 to the communication device 120 for synchronizing with clock 122. The synchronization of the clocks may occur just before initiation of the image capture period or with the initiation of the image capture period. The synchronization may occur once or may be repeated one or more times during the image capture period. In some embodiments, the synchronization of the clocks may be achieved by wired or wireless communication between the communication devices connected either directly or over a network.

In another embodiment, the medical system 100 is synchronized with the imaging system 118 by start and stop signals. The communication signal, including synchronization information in the form of a start signal, may be sent between the medical system 100 and the imaging system 118. The start signal may initiate, occur simultaneously with, or be triggered by the start the image capture period during which image data is recorded by the imaging system. The receipt or sending of the start signal may also initiate recording or mark a starting point in a longer recording of shape data for the instrument system 104 of the medical system 100. At the end of the image capture period, another communication signal, including synchronization information in the form of a stop signal, may be sent between the medical system 100 and the imaging system 118. The stop signal may initiate, occur simultaneously with, or be triggered by the stopping of the image capture period during which image data is recorded by the imaging system. The receipt or sending of the stop signal may also terminate recording or mark a termination point in a longer recording of shape data for the instrument system 104 of the medical system 100. In some examples, the start and stop signals are sent from the communication device 128 to the communication device 120 so that the imaging system 118 initiates and terminates the synchronization. In some examples, the start and stop signals are sent from the communication device 120 to the communication device 128 so that the medical system 100 initiates and terminates the synchronization.

Figure 7:
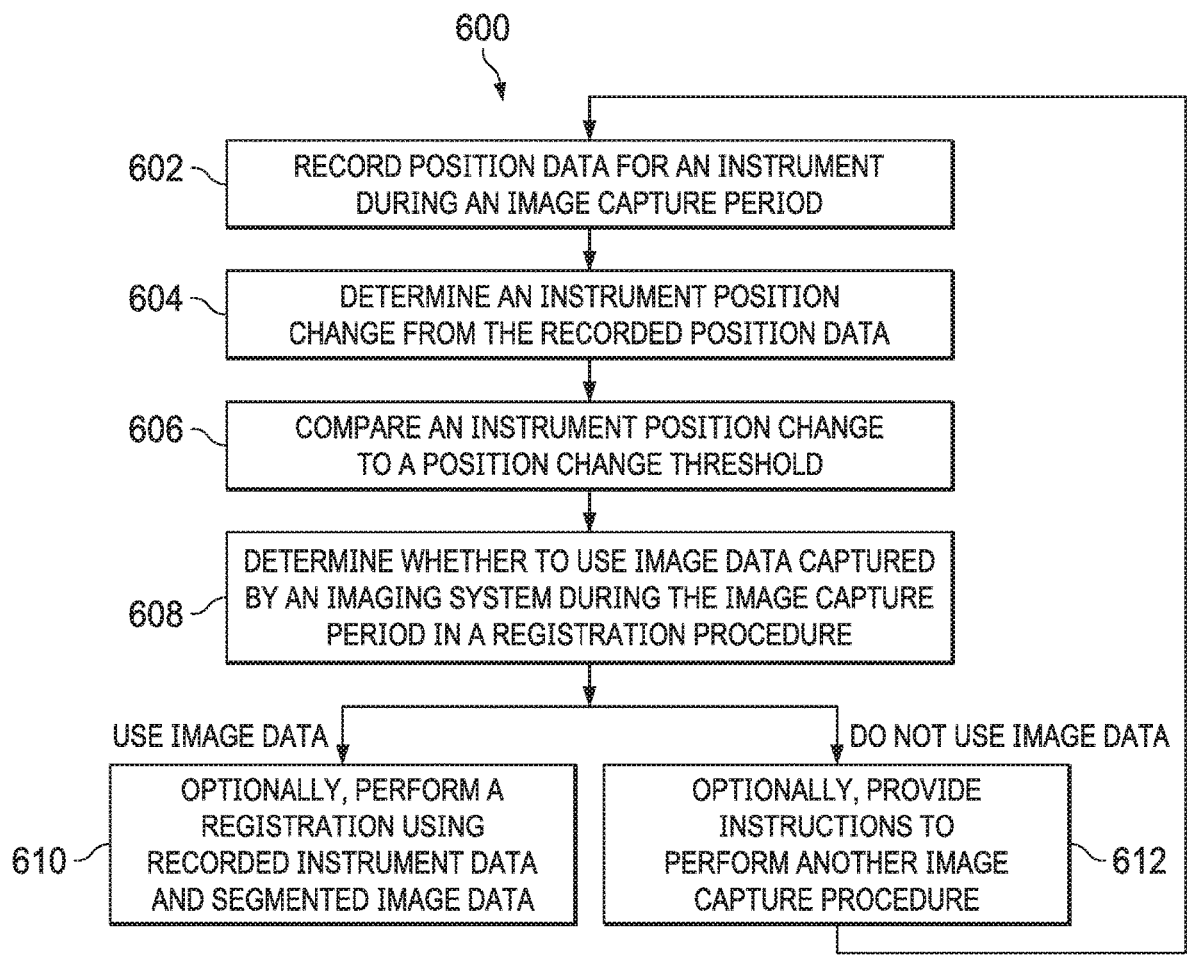
FIG. 7 illustrates a method for evaluating image data for use in a registration procedure.

In some embodiments, after the determination has been made to initiate the image capture as described in FIG. 4 and after the medical system and imaging system are synchronized as described in FIG. 5, a determination may be made as to whether the image data is suitable for use in registration. FIG. 7 illustrates a method 600 for evaluating anatomic image data for use in a registration procedure. Often, anatomical motion can result in intra-operative anatomical image data that is too distorted to isolate and segment the medical instrument. Before attempting to register the intra-operative image to the medical instrument, a change in the shape and position of the medical instrument may be evaluated over the image capture period. If the shape of the medical instrument changes in excess of a threshold amount, the captured image may be considered inadequate for use in registration, and instructions may be provided to initiate a new image capture procedure.

At a process 602, position data is recorded for an instrument (e.g., medical instrument system 104, 204) during an image capture period of an imaging system. In some embodiments, an image capture period corresponds to the time period during which an intra-operative imaging system 230 is activated to collect and record image data for a patient P. During that time period, position data for the instrument 204, located in the patient P, may recorded. For example, shape data, gathered from shape sensor 214, may provide position information for the instrument 204 and a plurality of points along the instrument 204 in the medical instrument reference frame $(X_M, Y_M, Z_M)$, which is known relative to the surgical reference frame $(X_S, Y_S, Z_S)$. During the time period, the instrument 204 may be subject to no commanded movement, such as operator-commanded advancement or bending, but may be subject to anatomical motion from breathing, cardiac activity, or other voluntary or involuntary patient motion. For example, an image scan may be performed with the intra-operative image system 230 over an image capture period while the instrument 204 is positioned within the patient P anatomy, without being subject to commanded motion.

At a process 604, a change in the instrument position during the image capture period is determined from the recorded position data. With reference to FIGS. 6A and 6B, in some embodiments, position and orientation data for a set of points S, corresponding to the shape of the instrument 204 in the medical instrument reference frame ($X_M$, $Y_M$, $Z_M$), is gathered during the image capture period. Due to anatomical motion, the points S may have a configuration $S_{T1}$ at a time T1 during the image capture period and may have a configuration $S_{T2}$ at a time T2 during the image capture period. Thus, the shape and location of the instrument 204 may change during the image capture period due to anatomical motion. The magnitude of the change may be a quantified in any of several ways. For example, the change may be quantified as a maximum change in the position data. FIG. 6B illustrates a segment of the point set S. The distance D1 between a point A of set S at times T1 and T2 may be a maximum change for the point A. The distance D2 between a point B of set S at times T1 and T2 may be a maximum change for the point B. In some embodiments, the position change for the points in the segment nearest to the distal end of the instrument 204 may be of primary interest in determining the maximum change. In some embodiments, the instrument position change may be determined from an average change in position for the points of the point set S. In some embodiments, the instrument position change may be determined from standard deviation in the position data for the points in the point set S. A determined position change may be based on a change for the entire set of point S or for segments of the set of points S. The position change may be determined in one, two, or three dimensions or a combination thereof.

At a process 406, the determined position change is compared to a position change threshold. For example, if the determined position change is 1 cm and the position change threshold is approximately 2 cm, the change in position does not reach the threshold. If the determined position change is 3 cm and the position change threshold is 2 cm, the change in position has exceeded the threshold. In some embodiments, the position change threshold may be established in one, two, or three dimensions or a combination thereof, with the same or different threshold values in the different dimensions. In some embodiments, the comparison may also include comparisons of orientation and shape. In various embodiments, the position change threshold may be greater or less than 2 cm. In various embodiments, the position change threshold may be a threshold based on, for example, a maximum position change, an average position change, or a standard deviation for the position change.

At a process 608, a determination is made as to whether the image data captured by the imaging system during the image capture period may be used in a registration procedure to register the image reference frame ($X_I$, $Y_I$, $Z_I$) to the medical instrument reference frame ($X_M$, $Y_M$, $Z_M$) and/or the surgical reference frame ($X_S$, $Y_S$, $Z_S$). If the instrument 204 is determined to have moved too much (e.g., in excess of the position change threshold), discrepancies between the image data from the intra-operative imaging system 230 and the shape data from the instrument 204 may prevent registration of the image reference frame ($X_I$, $Y_I$, $Z_I$) to the medical instrument reference frame ($X_M$, $Y_M$, $Z_M$) and/or the surgical reference frame ($X_S$, $Y_S$, $Z_S$). In this case, a determination would be made to not use the image data for a registration procedure. For example, if the change in instrument position is 3 cm, exceeding the position change threshold of 2 cm, this may indicate that instrument 204 moved too much during the image capture period, and the image data generated by the intra-operative imaging system 230 may be too distorted to provide an accurate registration to the instrument shape data S gathered during the image capture period. If, however, the change in instrument position is 1 cm, below the position change threshold of 2 cm, this may indicate that the movement of the instrument 204 was within an acceptable range, and the image data generated by the intra-operative imaging system 230 may be used for registration. In some embodiments, control signals sent to the instrument may be evaluated to determine if commanded movement, such as operator-commanded advancement or bending, occurred during the image capture period. If a determination is made that commanded motion did occur, the image data may be discarded, suppressed or otherwise not used for registration.

At an optional process 610, if the image data is determined to be acceptable for use in registration, the registration may be performed. In some embodiments, as part of a registration process, image units, such as pixels or voxels, in the image data from the imaging system 230 that correspond to the medical instrument 204 are identified. In some embodiments, computer software, alone or in combination with manual input, is used to convert the image data into a segmented two-dimensional or three-dimensional composite representation or model of a partial or an entire anatomic organ or anatomic region. The model may describe the various locations and shapes of the anatomic passageways and their connectivity. More specifically, during the segmentation process the pixels or voxels may be partitioned into segments or elements or be tagged to indicate that they share certain characteristics or computed properties such as color, density, intensity, and texture. The image data corresponding to the image of the medical instrument may be segmented or filtered out of the image data, and a model of the instrument shape may be generated. For example, the medical instrument 204 may be identified as a medical instrument in the image data by the segmentation or filtering by CT number or Hounsfield value associated with the medical instrument 204. This data associated with the medical instrument 204 may be isolated from other portions of the image data that are associated with the patient P or with specific tissue types. A three-dimensional mesh model may be formed around the isolated data and/or a centerline may be determined that represents a centerline of the medical instrument. The segmented image data for the instrument 204 may be expressed in the image reference frame ($X_I$, $Y_I$, $Z_I$).

The segmented shape of the medical instrument 204 may be registered with the shape data obtained from the medical instrument 204 during the image capture period. The shape data from the medical instrument may be expressed in the medical instrument reference frame ($X_M$, $Y_M$, $Z_M$) and/or the surgical reference frame ($X_S$, $Y_S$, $Z_S$). This registration may rotate, translate, or otherwise manipulate by rigid or non-rigid transforms points associated with the segmented shape and points associated with the shape data. This registration between the model and instrument frames of reference may be achieved, for example, by using ICP or another point cloud registration technique. In some embodiments, the segmented shape of the medical instrument is registered to the shape data and the associated transform (a vector applied to each of the points in the segmented shape to align with the shape data in the shape sensor reference frame) may then be applied to the entire three-dimensional image and/or to subsequently obtained three-dimensional images during the medical procedure. The transform may be a six degrees-of-freedom (6DOF) transform, such that the shape data may be translated or rotated in any or all of X, Y, and Z and pitch, roll, and yaw.

With the image reference frame ($X_I$, $Y_I$, $Z_I$) registered to the medical instrument reference frame ($X_M$, $Y_M$, $Z_M$), the images displayed to the operator O on the display system 110, may allow the operator to more accurately steer the medical instrument, visualize a target lesion relative to the medical instrument, observe a view from the perspective of a distal end of the medical instrument, and/or improve efficiency and efficacy of targeted medical procedures.

In some embodiments, the intra-operative image data may be registered with pre-operative image data obtained by the same or a different imaging system. Thus, by registering the shape data to the intra-operative image data, the registration of the shape data to the pre-operative image data may also be determined. In some embodiments, an anatomic image generated from the intra-operative image data and/or the pre-operative image data may be displayed with the image of the instrument 204, derived from the instrument shape sensor data. For example, a model of the instrument 204 generated from the instrument shape data may be superimposed on the image of the patient anatomy generated from the image data.

At an optional process 612, if the image data is determined to be unacceptable for use in registration, the registration procedure may be aborted. Instructions may be provided to a user to initiate a new image capture procedure or the control system may initiate the new image capture procedure.

Figure 8:
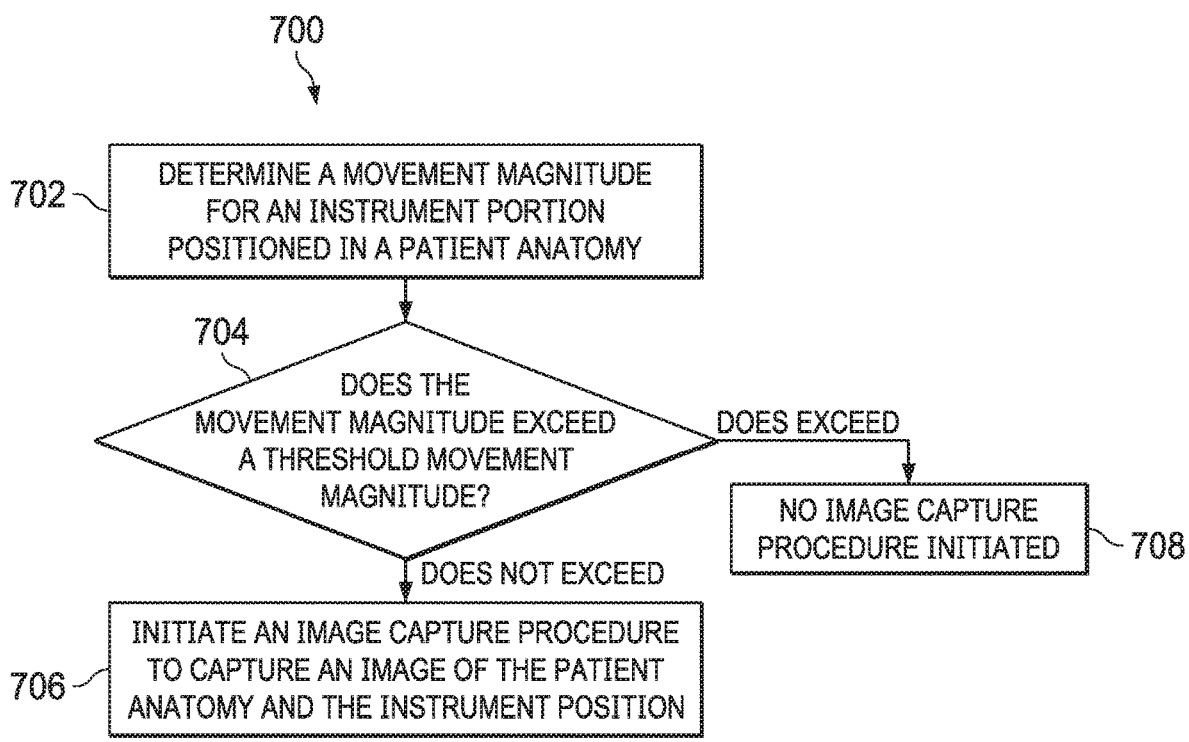
FIG. 8 illustrates a method for evaluating anatomical motion.

In some embodiments, prior to initiating an image capture procedure, a determination may be made as to whether the instrument or a portion of the instrument in the proximity of an anatomic target (e.g., a lesion or nodule) is in an area where the anatomical motion (e.g., due to respiratory or cardiac processes) exceeds a threshold for suitable image capture. FIG. 8 illustrates a method 700 for evaluating anatomical motion. Often, anatomical motion can result in intra-operative anatomical image data that is too distorted to isolate and segment the medical instrument. Before capturing an intra-operative image to the medical instrument, a magnitude of anatomical motion may be evaluated. If the magnitude of anatomic motion exceeds a threshold amount, any captured images are likely to be distorted and may be considered inadequate for use in registration, and instructions may be provided to suspend image capture and/or to move the instrument to a different anatomical area.

At a process 702, a movement magnitude is determined for an instrument or a portion of an instrument (e.g., medical instrument system 104, 204) while the instrument is located in the anatomy of a patient P. For example, shape data, gathered from shape sensor 214, may be recorded for an instrument portion that would be in the field of view of the imaging system during an image capture procedure. The shape data may be recorded during a time period prior to initiation of an image capture procedure when the instrument portion is not subject to commanded motion. A movement magnitude may be determined by evaluating the change in the shape data during the time period.

At a process 704, a determination is made as to whether the movement magnitude exceeds a threshold movement magnitude. The threshold movement magnitude may be predetermined based on the magnitude of motion that will result in an unusable image. The movement threshold may be a measure of displacement, rotation, velocity, and/or other components of motion.

At a process 706, if the movement magnitude does not exceed the threshold movement magnitude, an image capture procedure may be initiated to capture an image of the patient anatomy and the instrument portion.

At a process 708, if the movement magnitude does exceed the threshold movement magnitude, an image capture procedure may be suspended. In some embodiments, a user may be instructed to suspend the image capture procedure or move the instrument to a different anatomical area.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

The methods described herein are illustrated as a set of operations or processes. Not all the illustrated processes may be performed in all embodiments of the methods. Additionally, one or more processes that are not expressly illustrated in may be included before, after, in between, or as part of the illustrated processes. In some embodiments, one or more of the processes may be performed by the control system. 112 or may be implemented, at least in part, in the form of executable code stored on non-transitory, tangible, machine-readable media that when run by one or more processors (e.g., the processors 114 of control system 112) may cause the one or more processors to perform one or more of the processes.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit, a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet. Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth. IrDA, HomeRF, IEEE 802.11, DECT, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

In some instances well known methods, procedures, components, and circuits have not been described in detail so as not to unnecessarily obscure aspects of the embodiments. This disclosure describes various instruments, portions of instruments, and anatomic structures in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Various aspects of the subject matter described herein are set forth in the following numbered examples.

Example 1: A non-transitory machine-readable medium comprising a plurality of machine-readable instructions which when executed by one or more processors associated with a computer-assisted medical system device are adapted to cause the one or more processors to perform a method comprising: recording position data for an instrument during an image capture period; determining an instrument position change from the recorded position data; comparing the instrument position change to a position change threshold; and based on the comparison, determining whether to use image data captured by an imaging system during the image capture period in a registration procedure.

Example 2: The non-transitory machine-readable medium of Example 1 wherein the position data includes position information for a plurality of points forming a shape of the instrument.

Example 3: The non-transitory machine-readable medium of Example 2 wherein determining the instrument position change includes determining a maximum change in the position information for the plurality of points.

Example 4: The non-transitory machine-readable medium of Example 2 wherein determining the instrument position change includes determining an average change in the position information for the plurality of points.

Example 5: The non-transitory machine-readable medium of Example 2 wherein determining the instrument position change includes determining a standard deviation for the position information for the plurality of points.

Example 6: The non-transitory machine-readable medium of Example 1 wherein comparing the instrument position change to a position change threshold includes comparing the instrument position change for a distal portion of the instrument to the position change threshold.

Example 7: The non-transitory machine-readable medium of Example 1 wherein determining whether to use the image data captured by the imaging system includes determining not to use the image if the instrument position change exceeds the position change threshold.

Example 8: The non-transitory machine-readable medium of Example 1 wherein determining whether to use the image data captured by the imaging system includes initiating the registration procedure if the position change threshold exceeds the instrument position change.

What is claimed is:

1. A system comprising:
a processor; and
a memory having computer readable instructions stored thereon, the computer readable instructions, when executed by the processor, cause the system to:
record position data for an instrument during an image capture period, wherein the instrument is moving during the image capture period;
determine an instrument position change for a distal portion of the instrument from the recorded position data;
compare the instrument position change to a position change threshold; and
based on the comparison, determine whether to use image data captured by an imaging system during the image capture period in a registration procedure, wherein determining whether to use the image data captured by the imaging system includes initiating the registration procedure if the instrument position change is less than the position change threshold.

2. The system of claim 1 wherein the position data includes position information for a plurality of points forming a shape of the instrument.

3. The system of claim 2 wherein determining the instrument position change includes determining a maximum change in the position information for the plurality of points.

4. The system of claim 2 wherein determining the instrument position change includes determining an average change in the position information for the plurality of points.

5. The system of claim 2 wherein determining the instrument position change includes determining a standard deviation for the position information for the plurality of points.

6. The system of claim 1 wherein the position change threshold is less than approximately 2 cm.

7. The system of claim 1 wherein determining whether to use the image data captured by the imaging system includes determining not to use the image data if the instrument position change exceeds the position change threshold.

8. The system of claim 7 further comprising providing an instruction to an operator of the imaging system.

9. The system of claim 1 wherein the position data for the instrument is recorded from an optical fiber shape sensor extending within the instrument.

10. The system of claim 1 further comprising the imaging system.

11. The system of claim 1 further comprising the instrument.

12. A method comprising:
recording position data for an instrument during an image capture period, wherein the instrument is moving during the image capture period;
determining an instrument position change for a distal portion of the instrument from the recorded position data;
comparing the instrument position change to a position change threshold; and
based on the comparing, determining whether to use image data captured by an imaging system during the image capture period in a registration procedure, wherein determining whether to use the image data captured by the imaging system includes initiating the registration procedure if the instrument position change is less than the position change threshold.

13. The method of claim 12 wherein the position data includes position information for a plurality of points forming a shape of the instrument.

14. The method of claim 13 wherein determining the instrument position change includes determining a maximum change in the position information for the plurality of points.

15. The method of claim 13 wherein determining the instrument position change includes determining an average change in the position information for the plurality of points.

16. The method of claim 13 wherein determining the instrument position change includes determining a standard deviation for the position information for the plurality of points.

17. The method of claim 12 wherein the position change threshold is less than approximately 2 cm.

18. The method of claim 12 wherein determining whether to use the image data captured by the imaging system includes determining not to use the image data if the instrument position change exceeds the position change threshold.

19. The method of claim 18 further comprising providing an instruction to an operator of the imaging system.

20. The method of claim 12 wherein the position data for the instrument is recorded from an optical fiber shape sensor extending within the instrument.

* * * * *